United States Patent [19]

Jones

[11] Patent Number: 4,977,245

[45] Date of Patent: Dec. 11, 1990

[54] METHODS AND COMPOSITIONS FOR INDUCING MONOCYTE CYTOTOXICITY

[75] Inventor: C. Michael Jones, Houston, Tex.

[73] Assignee: Board of Regents, The University of Texas System, Austin, Tex.

[21] Appl. No.: 917,983

[22] Filed: Oct. 10, 1986

[51] Int. Cl.$^5$ .................. C07K 15/00; A61K 37/00
[52] U.S. Cl. ................................. 530/35; 530/350; 530/395; 530/827; 424/85.1; 514/2; 514/8; 514/21
[58] Field of Search ............... 530/351, 350, 395, 827; 424/85.1, 85.2; 514/2, 8, 21

[56] References Cited

U.S. PATENT DOCUMENTS 4,722,998  2/1988  Canter et al. ...................... 530/351

OTHER PUBLICATIONS

Matthews, Eur. J. Immunol., 15, 1985, pp. 311–313.
Gregory et al., J. Immunol., 137(10) 1986, pp. 3231–3239 (abstract).
Meltzer et al., Fed. Proc., 41, 1982, pp. 2198–2205.
Jones et al. (1988), Immunobiol., 178:229–249.
Yoshida et al. (1975), Jrnl. Immunol., 114:915.
Broder et al. (1976), Jrnl. Clin. Invest., 58:1297.
Cohn (1978), Jrnl. Immunol., 121:813.
Gmelig-Meyling (1980), Jrnl. Immunol. Meth., 33:1.
Wiltrout et al. (1981) Manual of Macrophage Methodology, Marcel Dekker, Inc.
Okada et al. (1981), P.N.A.S., 78:7717.
Fischer et al. (1981), Cell. Immunol., 58:426.
Jones et al. (1981), Nature, 251:302.
Ralph et al. (1982), Cell. Immunol., 71:215 (Abstract only).
Le et al. (1983), J. Immunol., 131:2821.
Celada et al. (1984), J. Exp. Med., 160:55.
Eyster et al. (1983), N.E.J.M., 309:583.
Jones et al. (1984), Immunobiol., 167: Abstract No. 365.
Nathan et al. (1984), J. Exp. Med., 160:600.
Kleinerman et al. (1985), Cancer Res., 45:2058 (Abstract only).
Sadlik et al. (1985), Cancer Res., 45:1940 (Abstract only).
Proust et al. (1985), J. Immunol., 134:390 (Abstract only).
Jones et al. (1984), Immunobiol., 166:410.
Grillot-Courvalin et al. (1985) in T Cell Hybridomas, CRC Press, pp. 223–224.
Grabstein et al. (1986), Science, 232:506 (Abstract only).
Jones et al. (1986) J. Immunol., 137:571.
Daemen et al. (1986), Cancer Res., 46:4330.
Rosenberg et al. (1986) Science, 233:1318.
Goldstein et al. (1980), Cancer Res., 46:4315.

Primary Examiner—Garnette D. Draper
Attorney, Agent, or Firm—Arnold, White & Durkee

[57] ABSTRACT

The present disclosure relates to a new lymphokine molecule, referred to as Monocyte Cytotoxicity Inducing Factor (MCF), and its use as in cancer and other types of therapy. The disclosure further relates to the development of novel Sezary cell hybridomas which secrete MCF and thereby provide a ready source for MCF isolation and purification.

Sezary'is Syndrome i a leukemic proliferation of OKT4+ lymphocytes. Sezary cells were isolated by differential centrifugation and fused to CEM.8aza.$^r$C, an HGPRTase lacking clone of CEM. The hybrid cells were studied for their ability to produce soluble mediators of human monocyte cytotoxicity. The product of a single clone, FtF3, which bore the surface phenotype of Sezary cells, was characterized. Monocyte cytotoxicity inducing factor was found to be stable at pH 2 for one hour, unlike interferon-gamma, and was found to be more heat stable as well. Moreover, treatment of MCF with antisera to interferons gamma, alpha, or a combination of gamma and alpha failed to neutralize its biologic activity.

MCF binds to Matrex Gel Red A. MCF eluted from this dye-ligand was found to have an apparent molecular weight of 11,500 Daltons by gel filtration and 14,700 Daltons by SDS-polyacrylamide gel electrophoresis.

MCF produced by hybridized Sezary cells appear to be neither interferon-gamma nor an altered molecular form of interferon-gamma, yet is a potent inducer of human monocyte cytotoxicity.

7 Claims, 2 Drawing Sheets

METHODS AND COMPOSITIONS FOR INDUCING MONOCYTE CYTOTOXICITY

The government may own certain rights in the present invention pursuant to NIH grant R23-CA39441-01.

BACKGROUND OF THE INVENTION

1. Field of the Invention

The present invention is directed to biological compositions and methods for inducing human monocytes to a cytoxic state. More particularly, the present invention relates to a soluble factor which induces monocyte cytotoxicity and antitumor activity.

2. Description of the Related Art

Immune protection of vertebrates is provided by a dual system that maintains two basic defenses against foreign invaders. These two defenses, termed cellular and humoral immunity, are adaptive and respond specifically to most foreign substances, although one response generally is favored. While cellular immunity is particularly affective against foreign tissue, cancer cells, intracellular viral infections and parasites, the humoral immune response defends primarily against the extracellular phases of bacterial and viral infections. Therefore, the cellular response is directed primarily against invading cells, while the humoral response is directed against primarily cell products, such as toxins. Moreover, whereas cellular immunity is provided by cells of the lymphoid system, humoral immunity is provided by proteins called antibodies that circulate through the fluid compartments of the body.

The dual nature of the immune system is generated, from two separate populations of morphologically indistin guishable lymphoid cells called lymphocytes. While one class of lymphocytes, the T-cell lymphocytes, mediate the cellular immune response, the other class of lymphocytes, the B-cells, are responsible for the humoral immune response. Thus, when the organism is invaded by a foreign substance, for example an altered cell (e.g.—viral transformed cell or tumor cell), some of the T-cells that recognize it are activated and initiate reactions that include binding to and eliminating the altered cells. On the other hand, when individual B-cells are activated, they differentiate to plasma cells that secrete specific antibodies directed against substances secreted by the foreign invader. For a good review of the foregoing, see Hood et al., *Immunology*, Second Edition, 1984, Benjamin/Cummings Publishing Company, Inc., Menlo Park, Calif.

While cells of B-lymphocyte lineage have found widespread clinical and industrial application in the generation of monoclonal antibodies, cells of T-lymphocyte lineage have proved of interest in part due to the numerous soluble factors they secrete. In the biologic system, T-cell factors play an important role in modulating and activating various immune functions. Isolation and characterization of various T-cell factors has been the goal of many clinical research endeavors attempting to identify those factors which might be useful in treating a number of disease states, for example, in the treatment of tumor cells and viral infectious states. Of particular interest has been the recent characterization of a factor termed T-cell growth factor, or interleukin II, which is produced and secreted by effector $T_A$ cells. (See U.S. Pat. Nos. 4,401,756; 4,404,208; 4,407,945; and 4,473,642). When $T_C$ cells are stimulated by interleukin II, they undergo an effector phase and are stimulated to mature into killer T-cells which are capable of identifying and eliminating various target cells. As demonstrated by the above patents, interleukin II has become an important pharmaceutical agent in the treatment of various disease states.

Optimism spurred by the preliminary success of interleukin II have lead researchers on a quest to identify other immune-mediating factors having potential clinical applicability. However, this search has generally been hampered by the existence of numerous factors secreted by the same or similar cell types. Moreover, confusion often results from the general overlapping nature of the factor activities and often times from a lack of currently available test systems for identifying individual factor activities. Without highly sensitive test systems for identifying individual factor activities, the existence of a particular factor cannot be readily distinguished from other factor activities.

Recently, interest has been shown in identifying soluble factors which serve to stimulate human monocyte cytotoxicity. Monocytes are a phagocyte of the blood which, along with macrophages and polymorphonuclear leukocytes, bind and ingest foreign substances often prior to an antibody response. "Activated" monocytes have recently been shown to exert an antitumor activity. For example, Fischer et al. (*Cell. Immunol.*, 58:426–435 (1981)) disclose that human peripherial blood monocytes can reproducably lyse a variety of tumor cells. More recently, researchers have disclosed various factors thought to play a role in monocyte activation. For example, Kleinerman et al. (*Cancer Res.*, 45:2058–2064 (1985)), discusses the activation of human blood monocytes by incubation with concanavalin A-stimulated lymphokine (macrophage-activating factor (MAF)), lipopolysaccharide endotoxin, and human recombinant gamma interferon. It was reported that gamma interferon, in the presence of endotoxin, was capable of activating monocyte tumoricidal activity. Moreover, MAF treatment exhibited a similar effect.

Other monocyte cytotoxicity promoting factors have been identified as well. For example, Le et al. (*J. Immunol.*, 131:2821–2826, 1983) has reported a T-cell hybridoma line capable of producing a macrophage activating factor with the ability to activate human blood monocytes to show enhanced cytotoxicity against a human colon adenocarcinoma line. However, this activity was found to be neutralized with specific antiserum to purified human interferon-gamma. These authors concluded that this MAF was in fact interferon-gamma.

More recently, Jones and Clouse (*Immunobiol.*, 167: Abstract No. 365 (1984)) reported the use of lymphocytes from patients with Sezary's syndrome in the production of a human T-cell hybridoma line which is capable of producing a factor which stimulates monocyte antitumor cytotoxicity. In contrast to the factor identified by Le et al., the factor reported in the Jones and Clouse publication was not inhibited by antibodies having specificity for interferon-gamma. Although the Jones and Clouse reference did observe that two molecular weight species having the biologic activity was observable, the methodology used to identify this particular activity was not identified. Moreover, the methodology for identifying and isolating Sezary/T-cell hybridomas which secrete the particular factor was not disclosed. Clearly, not all Sezary/T-cell hybridoma are capable of producing monocyte stimulatory factors (See, e.g., Grillot-Courvalin et al., "Helper T-

Hybridoma Produced By Fusion With Sezary Cells," in: *T-Cell Hybridomas*, ed. by M. J. Taussig, CRC Press, Inc., Boca Raton, Fla., 1985).

It is apparent from the foregoing references that, not only are there numerous factors potentially involved in the stimulation of monocyte cytotoxicity, but additionally that these factor activities may be indistinguishable in previously available assays for detecting various cytotoxic actions.

Accordingly, the present invention is directed to methods for accomplishing the isolation of particular discrete soluble factors which exhibit monocyte cytotoxicity inducing activity. Moreover, the present disclosure is directed to a detailed characterization of these factors and to the preparation of T-cell hybridoma lines which produce these factors in vitro and thereby provide a ready source for isolating the factors. In that the novel factors of the present invention demonstrate a surprising ability to elicit an antitumor response in vitro, similar to that possessed by interleukin II, it is believed that these factors will provide an important new addition to the antineoplastic armament of medical science.

SUMMARY OF THE INVENTION

The present invention is directed to a composition which includes substantially purified human mondyte cytotoxicity inducing factor, also referred to herein as MCF. The composition includes a substantially purified soluble factor capable of inducing human monocytes to a cytotoxic state, the factor having a molecular weight of between about 18,100 and about 14,700 Daltons when determined by polyacrylamide gel electrophoresis under the conditions as described herein. It will be appreciated that under differing electrophoresis conditions, this molecular weight may vary. When subjected to gel filtration chromatography, the factor has an apparent molecular weight of approximately 11,500 Daltons when chromatographed under the conditions described herein. Again, as with gel electrophoresis, it will be appreciated that gel filtration chromatography does not provide an exact molecular weight determination, rather such molecular weight determinations appear as a broad elution of monocyte cytotoxicity inducing activity, wherein the peak activity elutes from such columns at a position which corresponds to approximately 11,500 Daltons. However, this molecular weight may vary with variations in conditions, for example, running buffer, exclusion limit, column size and the particular gel filtration methodology which is utilized.

The present invention is additionally directed to a substantially purified soluble factor capable of inducing human monocytes to a cytotoxic state wherein the factor exhibits a molecular weight of between about 78,400 and about 63,600 Daltons by gel electrophoresis chromatography and, further, essentially co-eluting with bovine serum albumin by gel filtration chromatography. In that bovine serum albumin has a molecular weight of approximately 68,000 Daltons, the molecular weight of this factor as determined by gel filtration chromatography is substantially similar to the molecular weight determined by polyacrylamide gel electrophoresis.

A composition which includes one or both of the above factors may be further characterized by physicochemical and biologic characteristics. For example, the composition and factor(s) retains biologic stability following treatment at pH2 for one hour. The term biologic stability, as used herein, is defined as the retention of substantial biologic activity following the indicated treatment as defined by the present disclosure. The composition similarly retains biologic stability following of treatment at 60 degrees Centigrade for one hour and further retains biologic activity in the presence of antiserum to interferon-gamma, interferon-alpha, or a combination antisera to interferon-alpha and gamma.

The present invention is additionally directed to a continuous cell line which produces a factor as defined by the foregoing characteristics. In particular, a continuous cell line is provided which produces a factor capable of inducing human monocytes to a cytotoxic state, wherein the cell line is produced by a process which includes the steps of immortalizing human T-cells to produce continuous cell clones; identifying a clone which produces the factor; and culturing the clone to provide the continuous cell line.

The first step of immortalizing human T-cells to produce continuous cell clones is generally defined as providing human T-cells in a manner whereby they may be cultured continuously for an indefinite period. The most convenient manner for providing such continuous cell clones is through the development of a T-cell hybridoma. T-cell hybridomas are generally well known in the art and may be generated by a variety of well known methods. In general, such methods include fusing human T-cells with a second cell population which is sensitive to growth in a selective media and culturing the fused cells in the selective media to produce the continuous cell clones. Cells may be fused in numerous ways, for example, through the use of polyethylene glycol or sendai virus.

In a preferred embodiment, the second cell population is a T-cell lymphoma population which has been selected for growth in 8-azaguanine. By selecting for T-cell lymphomas capable of growth in 8-azaguanine, a cell population sensitive to growth in HAT selective media is obtained. Those of skill in the art will recognize that other cell lines having other selective criteria may be utilized for fusion with human T-cells to provide the continuous cell clones. For example, additional T-cell lymphoma subtypes could be used to clone other subclasses of human T-lymphocytes. Moreover, drug sensitivities and other selective criteria can be generated using other approaches including, 6-Thioguanine, oubaine or oncogenic transformation. Additionally, inter species hybrides can be generated to allow for chromosomal localization.

However, fusion is not the only means of achieving immortalized human T-cells. For example, certain human T-cells are responsive to T-cell growth factor and may be immortalized by continuous culturing in the presence of T-cell growth factor (interleukin II). Additionally, certain human T-cells, for example, certain neoplastic T-cell lines are capable of continuous growth in cell culture as are certain transformed (e.g.,—virus transformed) T-cell lines. While most T-lymphotrophic viruses are toxic, it is known that HTLV-1, as well as portions of the EB virus gerome, commonly utilized in B-lymphocyte transformation, can be used to transform and thereby immortilize, T-lymphocytes. All such continuously growing T-cells, and methods of providing continuously growing T-cells, are included within the scope of the present invention.

After obtaining the immortalized human T-cells in the form of continuous cell clones, a clone is identified which produces the monocyte cytotoxicity inducing factor. The crux of the successful practice of the present invention relies on the ability to identify clones which produce this factor rather than the numerous other immune regulatory and stimulatory factors known in the art. It is now believed that many hundreds of peptides, whose functions are unknown, are secreted by various activated T-cells. (see, e.g., Zurawski et al. (1986) *Science,* 232: 772-775). Moreover, depending on the particular T-cell which is immortalized, the number of clones positive for factor production may be quite low. Therefore, the assay must be not only highly specific for the present factor, but must be quite sensitive to the presence of small amounts of the factor, in order to successfully practice the present invention. Accordingly, the present disclosure is directed to an assay particularly adapted to identification of the present factor.

The final step of the present process is simply culturing the identified clone to produce the cell line. Where the immortalized human T-cell is achieved through hybridoma development, culturing will include simply culturing in an acceptable media. However, where the immortalized cell line does not involve cell fusion and instead requires the presence of a growth maintaining factor such as T-cell growth factor, culturing will require the inclusion of the particular growth factor.

In that it is believed that the factor of the present invention is secreted by a very small proportion of T-cells in general, it is a preferred embodiment of the present invention to employ Sezary cells as the T-cells to be immortalized. This is because it has been determined that a relatively large proportion of Sezary cells do in fact produce the present factor. However, in that it appears clear that not all Sezary cells produce the factor, the selection step is still required in order to identify clones producing the factor. However, if Sezary cells are unavailable, and one does not desire to screen the large number of clones which must necessarily be screened where T-cells in general are utilized, one may desire to use effector T-cells. It has been determined that a population of effector T-cells include a larger proportion of factor positive cells than due T-cells in general.

In a very general sense, the method of identifying a clone which produces the factor includes the steps of stimulating the clone with a T-cell mitogen to release lymphokines; culturing human monocytes together with appropriate target cells, for example, human cancer cells, in the presence of the released lymphokines; and detecting target cell lysis, wherein such lysis is indicative of the presence of human monocyte cytotoxicity inducing factor in the released lymphokines. As used herein, and as appreciated in the art, lymphokines is a generic term directed to any molecule having biologic activity for modulating the immune system. A T-cell mitogen, as will be appreciated by those of skill in the art, is a molecule or a compound having the ability to stimulate the release of lymphokines from T-cells. In a preferred aspect of the present invention, the T-cell mitogen used is phytohemagglutin, commonly referred to as PHA. However, conconavilin A and other T-cell mitogens known to the art may be successfully utilized.

The second step of culturing human monocytes together with appropriate target cells in the presence of released lymphokines allows for the specific induction of monocyte cytotoxicity inducing factor where such factor is present in the released lymphokines. As noted previously, this particular step is quite important to the successful practice of the present invention and is disclosed in detail in connection with the disclosure of a preferred embodiment in a later section. Of course, to demonstrate that the present factor is indeed effective against human target cells, an appropriate human target cell is preferred. A useful target cell has been identified as the human myeloid leukemic cell line, K562. However it is believed that numerous additional cell types may be employed, for example, melanoma, lung carcinoma and bladder cell tumors.

The final step of detecting target cell lysis is conveniently performed through the use of a radioisotope which is maintained extra or intracellularly when the target cell is in a non-lysed condition, and wherein the radioisotope is released into the surrounding media when the target cell is lysed. However, it will be appreciated that additional methods known in the art, and disclosed herein, may be used.

The present invention is additionally directed to a method for generating substantially purified monocyte cytotoxicity inducing factor which includes the steps of:

(a) stimulating a continuous cell line which produces the monocyte cytotoxicity inducing factor with T-cell mitogen to release the factor into the culture supernatant;
(b) subjecting the supernatant to gel filtration chromatography;
(c) assaying chromatography fractions for human monocyte cytotoxicity inducing activity; and
(d) collecting those fractions which exhibit the activity.

Practicing the method to this extent will provide a factor containing composition which is substantially purified with respect to biologic activity as defined by the disclosed assay. However, it is believed that sufficient biologic purity may be obtained by simply passing the culture supernatant over a Matrex Gel Red A (Amicon) column in a low salt-containing buffer to bind the factor to the Matrex gel, washing the column to remove nonbinding material, and eluting the bound fraction from the column with a high salt-containing buffer. Alternatively, to achieve an even more purified factor preparation, one may combine the gel filtration chromatography procedure with the Matrex gel red A column procedure. Even further purification may be obtained by combining either or both of the foregoing procedures with a polyacrylamide gel electrophoretic separation. It has additionally been determined that isolectric focusing techniques, which are generally well known in the art, provide for purification of MCF.

In that it is believed that the monocyte cytotoxicity inducing factor of the present invention will be clinically applicable in a manner similar to that identified for interleukin II and the various interferons, methods are additionally disclosed for clinical utilization and treatment of disease states using MCF. In addition to clinical applicability with respect to tumor treatment, as indicated by demonstrated in vitro efficacy in stimulating monocyte antitumor activity, it is believed that pharmaceutical compositions of the present invention will be useful in the treatment of infectious diseases, particularly those infectious diseases wherein the causative organisms reside in mononuclear phagocytes, for example, tuberculosis and leshmaniasis.

Additionally, it is believed that compositions included by the present invention will find diagnostic utility. Antiserum specific for MCF would be of value in determining blood levels of MCF, as well as documenting the ability of patients' mononuclear cells to produce MCF. Since MCF is produced by T-lymphocytes, and in particular, neoplastic T-lymphocytes, MCF will likely serve as a marker for diagnosis and/or evaluation of T-cell malignancies.

With respect to therapeutic utilization of MCF, one treatment protocol would include the ex vivo activation of a patients mononuclear cells for reinfusion into the patients in a manner analogous to LAK cells as described by Rosenberg et al. (*J. Natl. Cancer Inst.*, 75:595, 1985, and *N. Eng. J. Med.*, 313:1485, 1985). For direct delivery of MCF to tissue macrophages, it is contemplated that MCF may be given by direct transfusion, as well as being encapsulated in liposomes. Such techniques have recently been found to increase the efficacy and significantly prolong the half-life of related low molecular weight mediators. Liposome encapsulation can be accomplished in a number of manners, for example, as described by Fidler et al. (1976) *Cancer Res.*, 36:3608, incorporated herein by reference.

Additionally, combination therapy employing MCF in combination with interleukin II, interferon, tumor necrosis factor and cytoxan, are contemplated. These additional agents may be obtained and employed in a manner known in the art as further disclosed herein.

It is further believed that pharmaceutical compositions which include MCF will find utility in direct infusion treatment in a manner similar to that utilized for interferon treatment. It is believed that dosage determination, as well as proper infusion techniques, is well within the skill of the art as exemplified by Goldstein et al. (*Cancer Res.*, 46:4315–4329, 1986), incorporated herein by reference. Moreover, in that interferons have found applicability in the treatment of various infectious disease states as noted above, it is believed that such utility will be application to MCF as well, for example, when employed as suggested by Nathan et al (*J. Exp. Med.*, 160:600–605, 1984), incorporated herein by reference.

Diagnostic procedures, utilizing antibodies specific for MCF, may be employed in a manner similar to the current clinical test for acquired immune deficiency syndrome. Most conveniently, this would include a standard enzyme linked immuno sorbant assay (ELISA), well known to those skilled in the art.

DETAILED DESCRIPTION OF THE PREFERRED EMBODIMENTS

Introduction

Concepts of monocyte activation for cytotoxicity have undergone a change from the "all or none" paradigm to the more precise concept of a discrete stepwise process. Our present understanding of monocyte activation has been addressed by Cohn (*Jrnl. Immunol.*, 121:813–816, 1978). Moreover it is generally recognized that activation is regulated by products of T-lymphocytes. Soluble mediators of mononuclear phagocyte activation have recently been reviewed by Nathan et al., supra.

From these studies and earlier reports, interferon gamma would appear to the most important if not the only regulator of cytotoxicity against microorganisms and has recently been identified as a migration inhibitory factor. However, other studies have suggested that colony stimulating factor (CSF I), and the interferons alpha and beta, may have roles in regulating secretory or proliferative functions. The present invention is directed to the perhaps surprising discovery that an additional factor, termed monocyte cytotoxicity inducing factor (MCF) by the present inventors also plays a role. In light of the present finding, it is likely that additional factors will be identified through the development of the individual assays particularly suited to identification of factor activities.

The MCF disclosed by the present invention is characterized biologically by an ability to stimulate monocytes to a cytotoxic antitumor state. While the precise function of MCF within the biologic system is unknown, it is believed that it might play a role in affording specific activation of the cellular immune system. The factor is characterizable as having two molecular weight forms, a high molecular weight form of between approximately 63,600 and about 78,400 Daltons, or about the same molecular weight as bovine serum albumin, and a lower molecular weight form of between 11,500 and 18,100 Daltons, depending on the particular molecular weight determination method utilized. It is emphasized that these two molecular weight forms exhibit indistinguishable biologic activity in terms of monocyte activation. Therefore, the term MCF is meant to relate to either of these two molecular weight forms individually or in combination.

MCF is most conveniently isolated through the preparation of a T-cell hybridoma employing Sezary cells isolated from an individual having Sezary's syndrome. Sezary's syndrome is characterized by a proliferation of leukemic helper T-cells, and is discussed in some detail by Broder et al. (*J. Clin. Invest.*, 58:1297-1306, 1976). Sezary's cells circulate in the peripheral blood and are known to provide T-cell help for immunoglobulin production. These cells are identified by their characteristic cerebriform nuclei, PAS positive vacuoles, and additionally by their surface marker phenotype (OKT3+, OKT4+, OKT8−, OKIa1-(+)). Helper function has been defined by the ability of Sezary cells to stimulate polyclonal IgG production by B lymphocytes and by their production of MIF. Although lymphokine production does not necessarily segregate exclusively to any one subclass of T cells, Sezary's cells most probably represent a homogeneous clonal expression of one particular subclass of human T-lymphocytes which can be studied for production of lymphokine mediators uncontaminated by other T-cells.

The use of Sezary cells, as noted above, is not crucial to the practice of the present invention in that it is believed that MCF production is a feature common to lymphocyte populations in general. However, not all cells of a particular T-cell population produce MCF. Thus, where a general T-cell population is utilized, only a very small percentage of cells are likely to produce MCF. In the case of Sezary's cells, it appears as though MCF production is a more generalized phenomenon. Therefore, Sezary's cells are preferred in that T-cell hybridomas produced from Sezary's cells provide clones wherein there is a much greater likelihood that any one particular clone would produce MCF. Conversely, it is likely that when general T-cell populations are employed for hybridoma production, a substantial number of clones will likely have to be screened before a positive clone is identified. However, where Sezary's cells are not available, one may employ helper T-cells, in that it appears that helper T-cell populations contain a sufficient percentage of positive cells to avoid the exhaustive screening which would be necessitated by employing general T-cell lymphocyte populations.

Recently, strong evidence has been presented that interferon-gamma is the major mediator of macrophage/monocyte activation, and may be identical with the lymphokine macrophage activation factor (MAF). Interferon-gamma has also been described as the mediator of inhibition of mononuclear phagocyte migration and hence may be migration inhibition factor (MIF). However, it is known that activated Factor B of the alternative complement pathway (Bb), plasminogen activator (PA), and other products of monocytes will inhibit migration. Nathan et al., supra, have recently reviewed the range of mediators of mononuclear phagocyte activation.

The production of lymphokines by malignant T-cells is important in understanding host defense in conditions with chronic courses such as Sezary's syndrome and may reflect production of such mediators by non-malignant counterparts in the normal host. In developing the present invention, attempts were made to expand Sezary cells with interleukin II (IL-2), but these attempts were unsuccessful. Similar results have been reported by other groups, and have been attributed to the lack of IL-2 receptor expression or proliferation of Sezary cells by non-IL-2 dependent means. Clearly, as additional cell lines are screened for MCF production, cells will be identified which may be immortalized through the inclusion of growth factors in the cell growth medium, thus avoiding the need for hybridoma development.

Previously, hybridization has been utilized to perpetuate subclasses of murine T-cells and this technique was applied to Sezary's cells for the present invention. Other groups have employed Sezary cell hybridomas to study BCGF (B-cell growth factor) production by Sezary's cells. In the present invention, six cell lines were obtained by hybridization and all were capable of inducing human blood monocytes to become cytotoxic for the myeloid leukemia target, K562. For further study, one hybrid, FtF3, was selected whose phenotype (OKT3+, 4+, 8−, OKIII-, sIgG-) was identical to the parent Sezary's cell. It is on interest that all lines produced a lymphokine capable of inducing monocyte cytotoxicity (MCF). This probably results from positive selection of fusion partners since similar hybridization experience using whole murine T-cell populations have given rise to much smaller percentages of clones with MAF-like function.

Supernatants from PHA-stimulated FtF3 induced human mononuclear cytotoxicity but contained no detectable-interferon. Antisera to native interferon-gamma when added in excess to MCF having no antiviral activity produced only a 10–15% decrease in specific lysis of the target K562. Moreover, when formal titrations of the anti-IFN-gamma antisera were carried out using the constant antibody method previously described as being optimal for the detection of cross-reactivity with IFN-gamma, no neutralization titer could be determined. In contrast, treatment with the antisera to interferon-alpha caused a small increase in specific release. Addition of both antisera together produced no change in specific lysis. Both antisera were produced against partially purified native human interferons. In the case of the antisera to interferon-gamma, some cross-reactivity may be detected in that an MCF-like molecule could have been present in the preparation used to raise the antisera which was previously not recognized.

Recently, Schreiber has described the development of a series of monoclonal antibodies which are capable of differentially blocking antiviral or MAF activity of interferon-gamma, respectively. In particular, monoclonal antibodies directed against the C-terminus of recombinant interferon-gamma were reported to block MAF but not the antiviral activity of the recombinant interferon-gamma, while the antibodies to the N-terminus of recombinant interferon-gamma blocked antiviral but not MAF activity. Therefore, these findings could be consistant with an interpretation that MCF was an altered interferon species produced by a T-cell leukemia-derived hybridoma. However, the fact that MCF has recently been determined by the present inventors to be produced by normal effector T-cells, appears to rebut this theory.

These issues were further approached by direct comparison of the physicochemical properties of MCF and native interferon-gamma. Unlike interferon-gamma, MCF was stable at pH 2 but was partially inactivated at ph 8 and was much more stable than interferon-gamma. These findings would support the concept that MCF is not an altered interferon-gamma which has lost antiviral but not MAF activity, since interferon-gamma lost both MCF and anti-viral activity with both low pH and heat treatment.

Gel filtration chromatography of concetrated supernatants revealed two molecular weight species, one with a molecular weight of 64,000 Daltons which coeluted with the major protein peak, bovine serum albumin, and a second with a molecular weight of 11,500 Daltons. Although yields from our Bio-Gel P-100 column have been low, these values differ from the molecular weight of 50,000 reported for native human interferon-gamma when chromatographed under similar conditions.

MCF was found to bind to Matrex Gel Red A (procionred agarose; Amicon) and eluted with 1-N NaCl. Similar results have been reported for native interferon-gamma. MCF eluted from Matrex Gel Red A was electrophoresed under reducing conditions on a 10% SDS-PAGE gel. Two molecular weight species were identified. The first had a molecular weight between 78,400 and 63,600 Daltons and the second had a molecular weight of about 14,700 Daltons. The specific activity was 610 MCF units/mg protein and 1350 MCF units/mg protein, respectively. Yields from this procedure have been excellent with recoveries greater than 90%, despite treatment with SDS. This molecular weight differs significantly from those of 20,000 and 25,000 Daltons reported fro native interferon-gamma when electrophoresed under similar conditions.

Electrophoresis under reducing conditions followed by dialysis to remove SDS has resulted in each case in a diminution of biologic activity associated with the higher molecular weight form and greater recovery of the lower molecular weight form.

The following methods describe the preferred embodiment employing Sezary cells from two patients identified as having the syndrome. To achieve an immortalized Sezary cell line in the form of a Sezary/T-cell hybridoma, Sezary cells were fused with a T-cell lymphoma line conditioned in a manner to be sensitive to HAT selective media. The resulting hybridomas were found to produce MCF and were capable of being continuously cultivated. Culture supernatants were found to contain sufficient quantities of the MCF to allow for substantial purification through the utilization of techniques described herein.

EXAMPLES

1. Isolation of Sezary's cells

Mononuclear cells were isolated from 60 ml whole blood from a patient previously known to have Sezary's syndrome. Mononuclear cells were isolated by centrifugation over Ficoll-Hypaque (Pharmacia, Piscataway, N.J.). $7.5 \times 10^7$ cells having a phenotype of 87% OKT 3+, 77% OKT 4+, and 12% OKT 8+ were recovered from the F/P centrifugation and applied to a 35 ml gradient of Percoll (Pharmacia) according to the method of Gemlig-Meyling and Waldman (*J. Immunol. Method.*, 33:1, 1980, incorporated herein by reference). Briefly, the gradients were made by mixing 168 ml Percoll with 144 ml 2×PBS, and centrifuged for 40 min at $21,000\times$ g in a Beckman Model 71 centrifuge with a SS-34 fixed angle rotor. The cells were suspended in 5 ml of Hank's balanced salt solution (HBSS), layered gently on the gradient, centrifuged at $100\times$ g for 20 min at 20° C. in a swinging bucket rotor. Standard density marker beads (Pharmacia) were loaded on a companion gradient.

Three distinct "bands" were recovered from Percoll.

1. Field of the Invention At the interface between the Percoll and sample were $1.5 \times 10^6$ cells, the majority of which were polymorphonuclear leukocytes, and were discarded. Band I, 2 cm below the interface contained $1.9 \times 10^7$ cells which when studied by flow microfluorometry (FMF) were 90.2% OKT 3+, 80% OKT 4+, and 47% OKT 8+, and were morphologically small lymphocytes. Band II, located 5 cm below the interface contained $7.8 \times 10^6$ cells, which were 97% OKT 3+, 96% OKT 4+, and 17% OKT 8+. Microscopically, these cells were larger and had cerebriform nuclei. 38% of the total cells applied to the gradient were recovered.

Cells isolated in Band II were washed and resuspended at $5 \times 10^5$ cells/ml in RPMI 1640 with 10% fetal calf serum (FCS). Aliquots of these cells were cultured with 10 units/ml final concentration of interleukin II from the Gibbon ape cell line NLA-144. These cells failed to divide or incorporate 3H-Tdr after 72 hrs of culture thus demonstrating a lack of IL-2 responsiveness.

2. Preparation of 8-azaguanine Resistant T-lymphocytes

Since these particular Sezary's cells were not capable of indefinite sustained growth in tissue culture, it was decided to prepare a continuous T-cell hybridoma line by fusing the Sezary's cells with a T-lymphocyte population which has been conditioned to grow continuously in tissue culture. To achieve hybrid selectability, it was first necessary to select a cell population which was sensitive to HAT selection medium. This was accomplished through the preparation of an 8-azaguanine-resistant T-lymphocyte population.

It has been determined that certain commercially available T-lymphocyte cell lines are to be preferred over others. CCRF-CEM is a cell line obtainable from the ATCC (No. HB 9713) which, due to its apparent genetic stability, is to be preferred in generating hybridomas of the present invention. Two additional cell lines, MOLT and Jurkat, have been found to be genetically unstable upon drug selection and therefore unsuitable. However, the techniques of the present invention are applicable to any genetically stable T-cell lymphocyte or other cell type which can form a stable fusion product with T-cells and which is capable of continuous growth in culture. Determination of the foregoing criteria is within the skill of the art and the scope of the present disclosure is not limited to the preferred embodiment employing CCRF-CEM.

To generate 8-azaguanine resistant CCRF-CEM, cells were obtained from the American Type Culture Collection and grown in RPMI 1640 with 10% FCS. CEM was grown in increasing concentrations of 8-azaguanine primarily according to the method of Okada (*Proc. Natl. Acad. Sci.*, 78:7717, 1981, incorporated herein by reference). However, beginning with a concentration of 2 $\mu$M, the dose was doubled every 2 days until a dose of 16 $\mu$M was reached at which time the dose was doubled every 10 days until a dose of 100 $\mu$M was reached. After 6 weeks the cells were recloned and tested for their ability to grow in HAT-containing media (hypoxanthine, aminopterin, and thymidine), and subjected to FLOW microfluorometry.

3. Generation of T-cell Hybridomas

T-cell hybridomas were formed between Sezary cells, isolated as described in section 1 above, and the 8-azaguanine-resistant, HAT-sensitive CEM T-lymphocyte line (CEM.8aza$^r$. C), prepared as described in section 2 above. In particular, $7.5 \times 10^6$ cells from Band II of the Percoll gradient fractionation of patient's mononuclear cells were subjected to FLOW microfluorometry and light microscopic examination. These cells were hybridized to an equal number of CEM.-8aza$^r$.C using polyethylene glycol (mol wt 1000, Sigma, St. Louis, Mo.) as described by Jones, C. M., "T-cell Hybridomas producing Macrophage Activation Factors," In: T. Cell Hybridomas, Ed.: M. Taussig, CRC Press., Inc., Boca Raton, Fla., 1985, pp. 56–68, incorporated herein by reference. The fused cells were cultured for 24 hrs in RPMI 1640 with 10% FCS prior to addition of HAT-containing medium (hypoxanthine $1 \times 10^{-4}$M, aminopterin $4 \times 10^{-5}$M, and thymidine $1.6 \times 10^{-5}$M). Colonies were selected after 1 month in HAT media and cloned by limiting dilution.

Individual hybridoma clone colonies which were isolated by this procedure were adjusted to a culture density of $5 \times 10^5$ cells/ml and stimulated with 16 µg/ml phytohemagglutinin (PHA; Miles-Yeda, Rehovot, Israel) for 24 hours to stimulate lymphokine production. Thus, hybridoma clones were screened for positive MCF production by mitogen stimulation followed by subjecting the resultant hybridoma supernatants to biologic screening in the human monocyte cytotoxicity assay, which is discussed in detail below.

Figure 1:
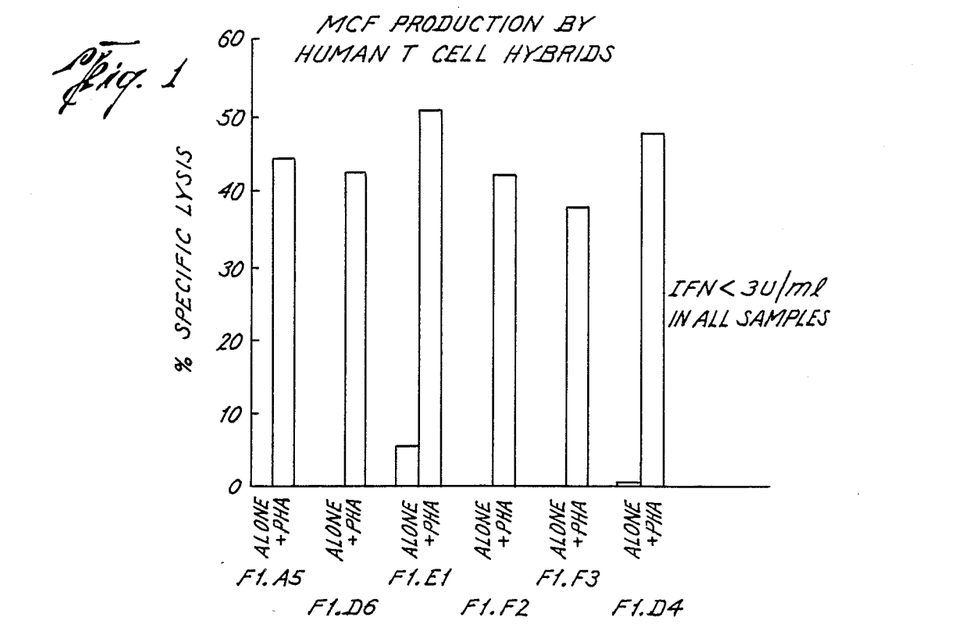
FIG. 1. Hybrid cells were adjusted to $1 \times 10^6$/ml and stimulated with 8 µg/ml PHA(+). PHA was added back to control (−) cultures, and both supernatants harvested by centrifugation. Monocyte cytotoxicity was measured as described herein with the exception that the monocyte monolater was incubated overnight to allow for decay of NK cell activity. The monolayer was incubated for a second 24 hr period with dilutions of MCF containing supernatants. Dilutions represented are ¼ in a total test volume of 0.2 ml. The supernatant was washed away and the $^{111}$In-Ox-labeled targets, K562 were added (E:T,30:1). Microtiter plates were centrifuged 16 hrs later, and supernatants collected and counted. % specific release was calculated as described herein.

In particular, supernatants of stimulated and unstimulated clones were incubated 20 hours with the monocyte monolayer. Serial dilutions of the supernatant were made to quantitate MCF in each sample. The data in FIG. 1 show that all six clones produce a factor(s) which induces human monocytes to kill K562. Their phenotypes were studied by FMF and two clones, FtF3 and FtA5, were uniformly OKT 3+, 4+, and were OKT 8− and OKT 1−, and IgG−.

Table 1 demonstrates the results obtained when supernatants from two representative MCF-producing hybridomas, FtA5 and FtF3, were subjected to the in vitro monocyte cytotoxicity assay. Cytotoxicity was measured by adding a fixed input of supernatant (25, 50 and 100 ml.) to a total test volume of 0.2 ml.

TABLE 1

| | Specific Cytotoxicity Induced By Hybridoma Supernatants | |
|---|---|---|
| Hybrid | Input (ul) | % Specific Lysis |
| FtA5 | 25 | 10.3 |
| | 50 | 25.1 ± 6.9 |
| | 100 | 38.3 ± 8.4 |
| FtF3 | 25 | 11.1 |
| | 50 | 26.2 ± 10.4 |
| | 100 | 37.7 ± 6.8 |

4. Human Monocyte Cytotoxicity Assay

As noted above, successful practice of the present invention rests on the ability to successfully identify MCF activity in an in vitro assay which has been designed to distinguish MCF activity from the numerous other lymphokine activities produced by T-cells. The assay described below has been derived in part from an assay method reported by Koren and his associates (Fischer et al., *Cell Immunol.*, 58:426, 1981). However, the assay as described in the Fischer et al. reference was found to be unacceptable in that it is not designed to measure lymphokine induced cytotoxicity and does not eliminate natural killer cell activity. It, therefore, must be modified as follows.

Human monocyte enriched leukopaks were obtained as a byproduct of the platelet donor program at M. D. Anderson Hospital, and were prepared with an IBM Model 2997 Cell Separator. Only healthy volunteer donors were used. All volunteer donors signed an informed consent, and the protocol was approved by the Committee for the Protection of Human Subjects, University of Texas Health Science Center. Mononuclear cells were prepared by centrifugation over Ficoll-/Hypaque. Monocyte monolayers were prepared by adherence to 96-well flatbottom plates previously coated with human serum as described by Golightly et al. (*Blood*, 61:390, 1983, incorporated herein by reference), and allowed to adhere to the serum coated plates for 15–30 mins followed by vigorous washing with warm (37° C.) Hank's balanced salt solution. This resulted in a confluent monolayer of >95% esterase positive cells. The monolayer was incubated overnight to allow for decay of residual natural killer activity before addition of lymphokine preparations on day 2. The monolayers were incubated with lymphokine for 20 hrs, washed, and the $^{111}$In-Ox labeled K562 added as targets.

The $^{111}$In-Ox labeled K562 target cells were prepared by the method of Wiltrout et al. (in: *Manual of Macrophage Methodology*, Ed. H. B. Herscowitz et al., Marcel Dekker, Inc., N.Y., 1981, pp 337–344, incorporated herein by reference). The effector to target ratio was 30:1. Spontaneous release averaged 15% (7–20%) in greater than 50 experiments. LPS (Lipopolysaccharide) free RPMI 1640 (M. A. Bioproducts, Walkersville, Md.) with 10% heat-inactivated AB-negative human serum (FLOW Laboratories, Arlington, VA) was used throughout the assay procedure. After 18 hrs incubation of monocyte monolayer with target, the plates were centrifuged and supernatant was removed and cpms were counted in a Beckman Biogamma 2000. Specific release was calulated as described by Wiltrout, Supra. Units of MCF activity were calculated as described by Lohmann-Matthes (Kniep et al. (1981), *J. Immunol.*, 127:417). 20% specific release equals 1 unit of MCF.

The primary distinction between the present assay and the one described by Fischer et al., is the finding that it is absolutely crucial that LPS-free media be utilized in order to distinguish the MCF activity from interfering activities. For the particular activity investigated by Fischer et al., the use of LPS-free media was not crucial in that it is noted by those authors that similar activities were observed regardless of whether LPS-free media was utilized. However, with respect to MCF, when LPS-containing media is used, a spontaneous release of label occurs and induction of lymphokine (MCF) directed cytotoxicity cannot be measured.

5. Deposit of Representative Sezary Cell Hybridomas with the American Type Culture Collection By the foregoing procedures, six hybridoma clones were identified whose supernatants exhibited MCF activity. Two were chosen for further physiochemical and biologic characterization. It has been determined that those two hybridomas, designated Ft.A5 and Ft.F3, both secrete the same MCF biologic profile, as determined by the characterization criteria disclosed herein. Accordingly, one of these hybridomas, Ft.F3, has been deposited with the ATCC and accorded ATCC reference number HB 9713.

6. Characterization of MCF

A. MCF is Antigenically Distinct From Interferon Gamma (1) Generation of MCF MCF was generated by stimulating $5\times10^5$, $1\times10^6$, $2.5\times10^6$, or $5\times10^6$ FtF3 or FtA5 cells/ml with 2, 4, 8, 16, or 32 ug/ml PHA (Miles-Yeda, Rehovot, Israel) in RPMI 1640 with 1, 2.5, 5, or 10% FCS (Hyclone, Sterile Systems, Logan Utah) for 24, 48, or 72 hrs. Unstimulated controls were grown with each to which an equal amount of PHA was added at the end of incubation. The cells were centrifuged, and the supernatants filter-sterilized, and stored at $-30°$ C. For characterization and purification, MCF was then prepared by stimulating $1\times10^6$ cells/ml in RPMI 1640, 1% FCS with 8 ug/ml PHA for 24 hrs, centrifuged, and filter sterilized. This routinely gave approximately 40 U/ml activity. Unstimulated controls to which PHA was added back were used in all experiments.

(2) Interferon Assay

Human interferon activity was measured as inhibition of plaque formation by Sindbis virus on WISH cells as described by Baron et al. (*Infect. Immun.*, 32:449, 1981). Sindbis virus, human alpha, beta, and gamma interferons were prepared by Drs. Samuel Baron and Marlyn Langford, University of Texas Medical Branch, Galveston, Tex. WISH cells were obtained from Drs. Baron and Langford. Using this plaque inhibition assay, interferon was not demonstrated in supernatants of FtF3 and FtA5.

(3) Treatment of IFN-gamma and MCF With Antisera to Various Interferons

Antibody to a partially purified preparation of native human gamma interferon (Langford et al. (1981), *J. Immunol.*, 126:1620), a 20 peptide N-terminal fragment of recombinant gamma interferon (Johnson et al. (1982), *J. Immunol.*, 129:2357) and human alpha interferon (Langford et al., supra) were prepared as described in the referenced articles. In initial experiments, 40 Units of MCF or 100 U IFN-gamma in 1 ml RPMI 1640, 1% FCS were incubated with 100 U of each of the antisera above alone or in combination at 4° C. for 30 min, 1 hr, and 4 hr. Following this incubation, serial dilutions of the IFN or MCF were made in RPMI 1640, 10% FCS and residual macrophage activating factor activity measured in the MCF assay.

27 U/ml of partially purified MCF were diluted ½ (13.5 U), ¼ (6.75 U), and ⅛ (3.375 U). Serial half-log dilutions were made of these dilute MCF, and the predicted number of units were confirmed by measurement in the MCF bioassay. Next, 27 U/ml of partially purified MCF were subject to serial half-log dilutions up to a final dilution of ⅛. 100 U, 50 U, or 25 U of each of the anti-IFN-gamma, antisera was added to each of these MCF dilutions and incubated for 1 hr at 25° C. Residual MCF activity was calculated in the constant antibody titration as recommended by Kawade (*J. Ifn. Res.*, 4:571-584, 1984). Units are expressed as described by Lohmann-Matthes (Kniep et al., supra).

Results from two representative sets of experiments are summarized in Table II. Anti-interferon-alpha produced no significant change in % specific release. On the contrary, the presence of this antisera during the activation has consistently produced small increases in specific lysis. The antibody to a partially purified preparation of native human interferon-gamma (SEA-activated human PBL) produced a decrease of only 15% and 10% specific lysis. Antisera to the 20-peptide N-terminal fragment of recombinant interferon-gamma or to a combination of interferons alpha and gamma failed to neutralize MCF. The antisera themselves produced only small changes in spontaneous release of label from the target K562 when added in place of the activating agent (spontaneous release=22.6% with media and monocytes alone; specific release= $-13.2\%$ with anti-IFN-alpha, $=4.66\%$ with anti-IFNY native, and $=8.4\%$ with anti-IFN-gamma N-terminus.) More importantly IFNgamma in amounts up to 1000 U/ml final concentration increased specific lysis only 6.2%. Since IFN-gamma did not produce significant activation for cytotoxicity in the present assay, direct comparison with MCF could not be performed.

TABLE II

| Treatment of MCF with Antisera | | |
|---|---|---|
| | % Specific Lysis | |
| Treatment | Exp 1 | Exp 2 |
| untreated | 54.6 ± 3.8 | 29.8 ± 5.4 |
| anti-IFN-alpha | 57.6 ± 5.0 | 35.8 ± 4.2 |
| anti-IFN-gamma (native) | 40.6 ± 3.8 | 19.9 ± 8.5 |
| anti-IFN-gamma N-terminus | | 26.5 ± 8.0 |
| anti-IFN-gamma (native) + anti-IFN-alpha | 48.8 ± 5.3 | |

In order to confirm that increasing concentrations of antibody relative to MCF units would not affect induction of cytotoxicity, the following experiments were performed. Serial checkerboard dilutions of 27 U/ml partially purified MCF were carried out as described above. In each experiment, 100, 50, or 25 U of the anti-IFN-gamma antibodies were added separately to MCF dilutions and residual MCF units were measured. The results summarized in Table III demonstrate that 100 U anti-IFN-gamma native reduced total bioassayable units by 7 U/ml. This is consistant with preceding experiments. Addition of 50 U/ml anti-IFN-gamma (native) and all inputs of anti-IFN-gamma N-terminus caused an increase in bioassayable units.

FtF3 and FtA5 MCF were also capable of activating murine peritoneal exudate macrophages for cytotoxicity against the target L5178Y. The presence of LPS did not appear to augment cytotoxicity induced by these lymphokines.

TABLE III

| Treatment of MCF with Anti-IFN-gamma by the Constant Antibody Technique | | |
|---|---|---|
| | MCF (units/ml) | |
| Input Ab (U/ml) | anti-IFNgamma (native) | anti-IFNgamma-N-terminus |
| 0 | 27 | 27 |
| 25 | 28 | 39 |
| 50 | 58 | 46 |
| 100 | 20 | 40 |

B. Physicochemical Characterization of MCF (1) pH Stability pH stability of MCF was compared to IFN-gamma by dialyzing 40 U MCF or 100 U IFN-gamma in Spectropor tubing (molecular weight cutoff of $5\times10^3$ Daltons) against 0.1M glycine-HCl, pH 2.0, 0.1M TRISHCl, pH 5.0, 0.15M PBS, pH 7.4, 0.15M PBS, pH 8.0, or 0.1M TRIS, pH 10.0 for 4 hrs at 25° C. The samples were then dialyzed against Dulbecco's PBS, pH 7.4, to restore neutrality prior to bioassay. IFNgamma was found to be totally inactivated at pH 2. However, as demonstrated by Table IV, MCF was found to be stable at pH 2. However, partial inactivation of MCF has consistantly been noted at pH 8.0.

TABLE IV pH Stability of MCF

| pH | % Specific Lysis |
|---|---|
| 2 | 41.7 ± 8.6 |
| 5 | 41.1 ± 6.4 |
| 7.4 | 36.8 ± 3.2 |
| 8 | 19.6 ± 4.6 |
| 10 | 45.4 ± 5.4 |

(2) Heat Stability of MCF

To test heat stability of MCF relative to IFN-gamma, forty units of MCF and 100 U IFN-gamma in 1 ml RPMI 1640/1% FCS were heated for 2 hrs in a constant temperature bath to study heat denaturization. As demonstrated by Table V, MCF was stable at temperatures up 60° C., but was totally inactivated at 100° C. IFN-gamma was not stable at temperatures higher than 4° C. for periods of 2 hrs or longer.

TABLE V

Heat Stability of MCF

| Temperature | % Specific Lysis |
|---|---|
| 4° | 53.3 ± 4.3 |
| 37° | 48.6 ± 4.9 |
| 60° | 48.0 ± 3.4 |
| 100° | 0.0 |

7. Purification of MCF

A. Gel Filtration of MCF

Gel filtration experiments were performed both to determine an approximate molecular weight and to begin preparation of a substantially purified fraction. 180 ml of MCF from PHA stimulated FtF3 supernatant ($7.2 \times 10^3$ U MCF) was concentrated 20-fold by pressure dialysis over an Amicon YM-10 membrane, applied to a 2.5×60 cm. column of Bio-Gel P100, equilibrated with PBS and eluted at a flow rate of 1.5 ml/min. 7.5 ml franctions were collected and were assayed undiluted, ½, and 1/5 for MCF activity. The column was calibrated with aldolase (158K), ovalbumin (45K), chymotrypsin (25K), and ribonuclease A (13.7K) (Pharmacia).

Figure 2:
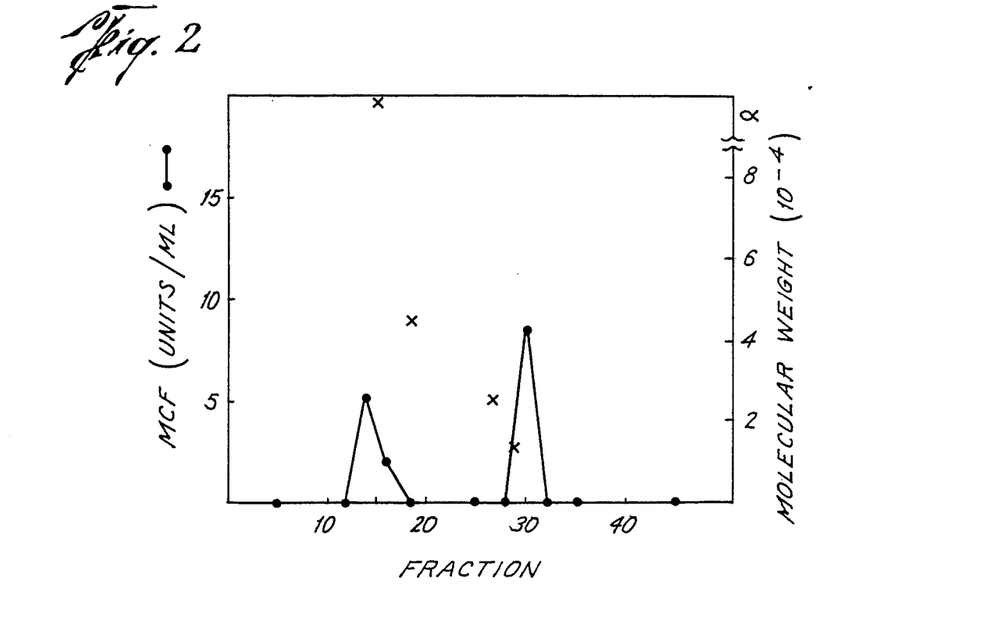
FIG. 2. $7.2 \times 10^3$ U of MCF in 28 ml was applied to $2.5 \times 60$ cm column of Bio-Gel P 100 equilibrated with PBS pH 7.4. The column was eluted at 1.6 ml/min and 7.5 ml fractions were collected. (−) MCF units/ml; (x) represent the molecular weight standards: ribonuclease A 13,700, chymotrypsinogen A 25,000, ovalbumin 45,000, and aldolase 158,000. Molecular weight determinations were calculated using Curvfit program (Interactive Microware, Inc. State College, Pa.) on an Apple II+ system.

The data in FIG. 2 demonstrated that two peaks of biologic activity were obtained. The first peak co-eluted with the major protein present, bovine serum albumin (from the fetal calf serum present in the culture media). The second peak of monocyte cytotoxicity inducing activity eluted in a region with an apparent molecular weight of approximately 11,500 Daltons.

B. Precipitation with Ammonium Sulfate

Initially, ammonium sulfate precipitation was attempted as a method for purification and concentration. MCF appeared to precipitate in the 30–50% range but resulted in greater than an 85% loss in biologic activity. Therefore, ammonium sulfate precipitation was not pursued further as a means for purification.

C. Binding of MCF to Matrex Gel Resins

Two ml of each of the Matrex Gel Resins (Amicon) was washed with 5M Urea and then washed with 20 ml PBS in 1.5M NaCl, pH 7.4. Four ml of FtF3 supernatant (160 U MCF in RPMI 1640, 1% FCS) was passed twice over each of the Matrex Gel Resins (Blue A, Red A, Orange A, Green A, and Blue B), washed with 2 volumes of starting buffer, and eluted stepwise with 1 volume each 0.5M NaCl. 1.0M NaCl, and 2 volumes 1.0M NaCl/ 50% ethylene glycol. The starting material, wash, and each fraction was then dialyzed at 4° C. for 24 hrs (Spectrapor tubing, $5 \times 10^3$ D molecular weight cut off) against 3 changes of PBS, pH 7.4, and then 4 hrs against distilled $H_2O$. The samples were placed in a glass tray and covered with Sephadex G-10 to reduce volume to approximately 1 ml. Each sample was then assayed for units MCF activity.

Figure 3:
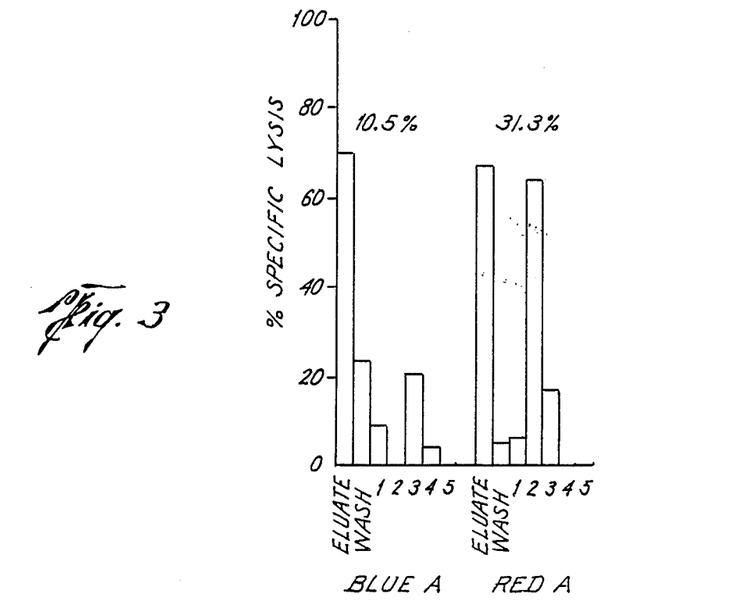
FIG. 3. 4 ml FtF3 supernatant was passed twice over 2 ml resin bed volume and eluted with a salt gradient. 10.5 and 31.3% activity could be eluted with 1-M NaCl on Blue A and Red A, respectively. Biologic activity was not recovered using Orange A, Green A, or Blue B.

MCF was bound and could not be eluted from Matrex Gels Orange A, Green A, and Blue B. However as summarized in FIG. 3, MCF bound to both Blue A, and Red A. Red A bound 31.3% of the starting material and eluted with 1.0M NaCl. Blue A bound only 10.5% of the starting and was not studied further. 175 ml of FtF3 supernatant/RPMI 1640, 1% FCS containing $7 \times 10^3$ units MCF was passed twice over a 2.5×30 cm column Matrex Gel Red A. The column was washed with two column volumes of starting buffer and eluted in a single step with 1.0M NaCl. The peak activity was present in fractions 11–14. Two×$10^3$ units in 20 ml (1.45 mg protein/ml) were collected. This preparative procedure resulted in a 2.5 fold concentration and gave a 28.5% yield. No IFN-gamma was detected in this preparation.

D. Polyacrylamide Gel Electrophoresis (PAGE)

To determine the molecular weight of MCF by an alternate procedure, samples having MCF activity were subjected to PAGE. In particular, 200 ul (20 U MCF/290 ug protein) prepared by chromatography over Matrex Gel Red A was mixed 1:1 with sample preparation buffer (0.0625 ml TRIS-HCl, 2% SDS, 5% 2ME, 10% sucrose, and 0.002% bromphenol blue), heated 3 min at 100° C., and centrifuged at high speed (1 min in an Adams microfuge). 100 ul aliquots were loaded into each of 4 lanes of a 1.5 mm thick SDS slab gel (BRL vertical gel apparatus, Gaithersburg, MD) using a 10% polyacrylamide gel, prepared according to Laemmli (*Nature,* 227:680, 1970), and run at 90 V through the stacking gel and 200 V through the running gel. The gel was cut into 1 cm slices, crushed, and eluted with 2 washes of 5 ml of PBS/0.1% SDS pH 7.4, for 12 hrs at 4° C. The samples were placed in a glass dish, and covered with Sephadex G-10 to reduce sample volume to 1.5 ml. Pharmacia standards prepared in the same buffer and run in companion lanes were used to determine molecular weight; phosphorylase B (94K), bovine serum albumin (67K), ovalbumin (43K), carbonic anhydrase (30K), soybean trypsin inhibitor (20K), and alpha-lactalbumin (14.4K). A companion gel was divided and stained with 1) Coomasie Brilliant Blue and 2) by a silver nitrate method (Oakley et al., *Anal Biochem.,* 105:361, 1980).

Figure 4:
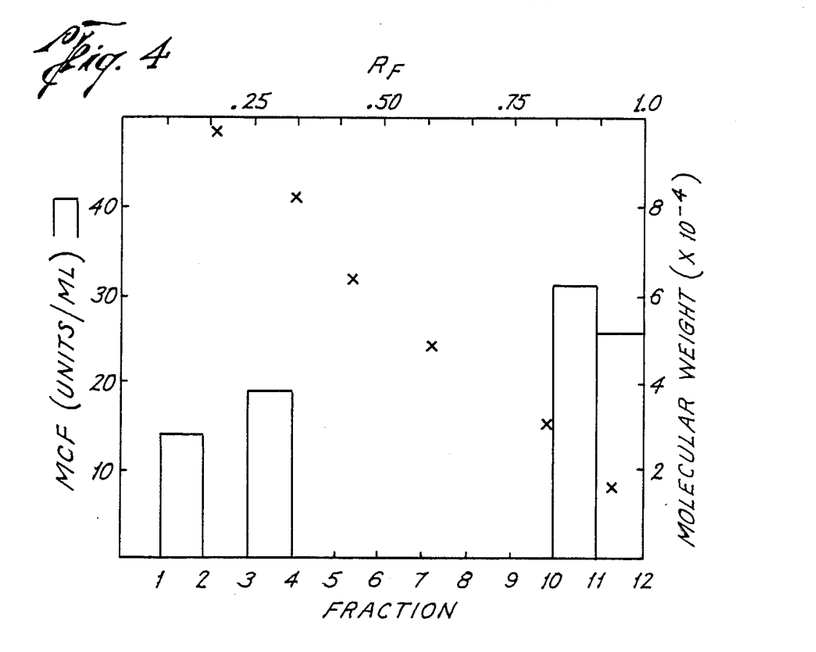
FIG. 4. 20 U of MCF/290 µg protein in 0.2 ml was mixed with sample buffer, heated, and centrifuged as described. 100 µl was loaded into each of 4 lanes of a 1.5 mm thick 10% polyacrylamide-SDS gel. After running at 200 V for 4 hrs, the gel was cut into 1 cm slices, crushed, eluted, and bioassayed. Companion lanes were stained by both Coomassie Blue and silver method. Molecular weight standards used were phosphorylase beta (94,000), bovine serum albumin (67,000), ovalbumin (43,000), carbonic anhydrase (30,000), soybean trypsin inhibitor (20,000), and .-lactalbumin (14,400). Molecular weight determinations were made using Ferguson plot analysis.

Two peaks of MCF activity were obtained, one with a molecular weight between 78,400 and 63,600 Daltons which was associated with a major protein band, bovine serum albumin (specific activity 610 U MCF/mg protein), and a second peak between 18,100 and 14,700 (specific activity 1350 U MCF/mg protein) (FIG. 4). Using a silver stain method, a protein band was detected associated with the major peak of MCF activity at 14,700 Daltons, which could not be detected using Coomassie Brilliant Blue. Recovery of biologic activity from the gel was greater than 90%.

TREATMENT PROTOCOLS

Due to precautions which are necessarily attendant to every new pharmaceutical, due both to consideration of patient safety and federal new drug regulations, the MCF of the present invention has not been tested as yet in a clinical setting in human subjects. However, the in vitro activity of MCF in stimulating monocytes to kill tumor cells, along with the recent clinical success of interleukin II, is believed to demonstrate the utility of the present invention in this regard. The following embodiments are therefore prophetic and represent the best mode contemplated by the present inventor of carrying out the practice of the invention in various clinical settings.

1. Antitumor Therapy

A. Direct Infusion

It is believed that MCF will prove to be useful in the treatment of various tumors, and in particular, tumors of the blood forming organs such as leukemias, or solid tumors which have been described as infiltrated by machrophages, by way of direct intravenous infusion of pharmaceutical compositions which include MCF. Such compositions would include effective doses of either MCF alone, or in combination with other therapeutic agents such as interleukin II, interferon, tumor necrosis factor or cytoxan. Interleukin II may be obtained as disclosed by numerous U.S. patents, including for example, U.S. Pat. Nos. 4,407,945 and 4,401,756, incorporated herein by reference. Cytoxan (cyclophosphamide) is a commercially available antineoplastic agent. Interferon is also commerically available as disclosed herein, and its clinical use has been reviewed and described in detail in numerous publications, including, for example, in Goldstein et al. (1986), *Can. Res.*, 46:4325-4329, incorporated herein by reference. Moreover, Goldstein discloses in detail the suggested and reported dose regimens for interferon antitumor therapy. Preparation of Tumor Necrosis Factor and its use is known in the art as exemplified by U.S. Pat. Nos. 4,457,916; 4,529,594; and 4,447,355 and as further disclosed by Carswell et al. (1975), *Proc. Natl. Acad. Sci, U.S.A.*, 72: 3666; Ruff et al. (1980), *J. Immunol.*, 125: 1671; Matthews et al. (1980), *Br. J. Cancer*, 42: 416; and Lu et al. (1986), *Cancer Res.*, 46(9): 4357, all of the foregoing references being incorporated by reference. Therefore, it is considered that use and dosages of MCF treatment, alone or in combination with these agents, is well within the skill of the art in light of the present specification.

MCF could be given daily by continuous infusion or given on alternative days with interleukin-2 or interferon being given on the other day. Such a treatment would be possible since the cytotoxic effect of MCF seems to last for about approximately 24 hours. Alternatively a large initial dose of Cytoxan could be given which should deplete suppressor T-lymphocytes followed by continuous infusion of MCF. Doses of MCF would of course have to be determined by experimental methods which are well known to skilled immunologists. However, dosages will likely be at least an order of magnitude lower than dosages of interferon gamma. Interferons are usually given as an IM dose of 3 million units thrice weekly although one would have to take into account whether total body water is being saturated. With a new agent of any type one would have to initiate a phase I trial first to establish levels at which unacceptable toxicity is reached.

B. Adoptive Immunotherapy

Adoptive immunotherapy is a new approach to treating metastatic cancer in which immune cells with anti-tumor reactivity are transferred to the tumor-bearing patient. Much of this work has been pioneered by Dr. Steven Rosenberg and is discussed in more detail in Resenberg et al. (1977), *Adv. Cancer Res.*, 25:323 and Rosenberg (1984), *Cancer Treat. Rep.*, 68:233, both incorporated by reference. In particular, interleukin II, also refered to as T-cell growth factor, has been shown to be a useful adjuvant to adoptive immunotherapy, wherein it is used to stimulate killer T-cell development (see, e.g., Rosenberg (1985), *J. Natl. Cancer Inst.*, 75:595, incorporated herein by reference). Moreover, adoptive therapy utilizing interleukin II has demonstrated applicability in the treatment of a variety of advanced metastatic cancers in humans (Rosenberg et al. (1985), *N. Eng. J. Med.*, 313:1485, incorporated herein by reference).

Accordingly, it is submitted that the MCF of the present invention can be utilized in an adoptive immunotherapy protocol in a manner similar to interleukin II. In particular, it is believed that the following proposed protocol will serve as a sufficient basis to teach those skilled in the art of adoptive immunotherapy to utilize MCF in this manner.

Monocytes will be harvested by cell separation using, for example, an IBM cell separator using accepted techniques. These cells would then be incubated with approximately 4 units/ml of MCF overnight followed by slow continuous infusion of the induced cells into the patients. Such therapy could initially be given 2 to 3 times a week. However, because of the long life span of monocytes it could perhaps be given at more infrequent intervals stretched over a much longer period to time to insure that infiltration into the tumor occurs.

C. Diagnostic Utility

MCF will additionally be of value as a clinical diagnostic aid. For example, antibodies having specificity for MCF will provide an ability to determine MCF blood levels, thereby assisting in maintaining therapeutic blood levels and perhaps in the diagnosis of T-cell malignancies which may be accompanied by high serum MCF levels. Moreover, MCF antiserum may be of use in evaluating T-cell function in normal individuals. Similar uses have been described for the so-called Melanoma-associated antigen.

The development of antibodies to a particular antigen whether polyclonal or monoclonal, are well known in the art and can readily be achieved by skilled immunologists. This is the case even where the particular molecule is not antigenic in and of itself, through either the attachment of an immunostimulating ligand such as keyhole limpet hacmocyanin, or by finding a species wherein the molecule is antigenic.

In the case of MCF it is believed that an antibody can readily be developed by either polyclonal or monoclonal approach. For examle, rabbits should be immunized with 100 micrograms of MCF in complete Freund's adjuvant into each of four sites and later boosted with MCF in incomplete Freund's adjuvant. Once a heteroantisera has been developed and quantitation determined by immunodot assay, western blotting, ELISA and various other immunodiagnostic techniques may be performed with such a hetero-antiserum. Monoclonal antibodies may be developed by a number of accepted techniques, for example, as disclosed by U.S. Pat. Nos. 4,172,124 and 4,271,145, both to Koprowski et al., incorporated herein by reference.

For in vitro diagnostic work, for example, in an immunoassay to quantitate serum MCF levels, the MCF antibody will be used most preferably in an ELISA assay which employs the antibody together with an immuno detection reagent capable of detecting quantitatively specific immune complex formation.

However, in general, immunodiagnostic kits would include reagents appropriate for either detecting patient-generated anti-MCF antibodies (e.g.-circulating antibodies) or detecting MCF, for example, tumor-generated MCF, in biologic fluids or tissues from patients. As used herein, a biologic fluid or tissue includes any fluid or tissue obtained from a patient, including, for example, urine, serum, plasma, and biopsy samples. In the case of MCF antibody-detection kits, such kits would include antigenically pure, and preferably titrated, MCF together with an immunodetection reagent. By antigenically pure MCF is meant an MCF preparation which does not substantially cross-react with non-MCF directed antibodies. Sufficient antigenic purification could be achieved through immunopurification by adsorption with normal sera or chromatography over anti-MCF antibodies as is known in the art.

In the case of MCF antigen detection kits, such kits would typically include antigenically pure, preferably titrated, anti-MCF antibody. By antigenically pure is meant antibody which will not substantially cross-react with antigens other than MCF. As with MCF antigen purification, polyclonal antibody purification could be achieved by immuno chromatography. However, a preferred antibody would be a monoclonal antibody.

In either case, immunodetection kits would include an immunodetection reagent for detecting and/or quantifying the occurrence of specific immunoreactions involving MCF. Typically such reagents include, for example, a radioactive or enzyme-linked ligand. Such ligands are typically associated w.th either the antibody, antigen or a second antigen or antibody. As noted, a preferred immunodetection system are the various systems based on the ELISA assay. For a further description of the ELISA assay and the various immunodetection reagents, please refer to U.S. Pat. Nos. 4,454,233 and 4,446,232, both incorporated herein by reference. It is believed that these patents provide sufficient disclosure to enable the use of antibody to MCF in a clinical immunoassay.

The present invention has been disclosed in terms of specific embodiments which are believed by inventor to be the best modes for carrying out the invention. However, in light of the disclosure hereby provided, those of skill in the various arts will recognize that modifications can be made without departing from the intended scope of the invention. For example, although the present invention is disclosed in terms of a Sezary cell hybridoma for MCF production, it is clear that other types of T-cells may be employed. Additionally, numerous embodiments are likely possible for isolation of the factor. Moreover, as biological characterization of the factor progresses, it is likely that more refined and simpler assays will be developed for MCF identification. For example, once an antibody to MCF has been developed, such antibody can be used directly to assay for MCF production by the various cell populations. These and all other modifications and embodiments are intended to be within the spirit and scope of the present invention and appended claims.

What is claimed is:

1. A substantially purified human monocyte cytotoxicity inducing factor characterized by the following properties:
   (a) capable of inducing human monocytes to a cytotoxic state;
   (b) an apparent molecular weight of approximately 11.5 kilodaltons as determined by gel filtration chromatography;
   (c) an apparent molecular weight of between about 18.1 and about 14.7 kilodaltons as determined by SDS polyacrylamide gel electrophoresis;
   (d) retention of biologic activity following treatment at pH 2 for one hour;
   (e) retention of biologic activity following treatment at 60° C. for one hour;
   (f) ability to bind to matrex gel red A under low salt conditions and elute from Matrex gel red A under high salt conditions; and
   (g) retention of biologic activity in the presence of antiserum to interferon gamma, interferon alpha, or a combination of antisera to interferon alpha and gamma.

2. The factor of claim 1, further defined as being dispersed in an aqueous composition having a biologic activity of up to about 100 MCF units/ml of the composition.

3. The factor of claim 2, wherein the aqueous composition has a biologic activity of up to about 40 MCF units/ml of the composition.

4. The factor of claim 1, further defined as having a biologic activity of up to about 1350 MCF units/mg protein.

5. The factor of claim 4, further defined as having a biologic activity of up to about 69 MCF units/mg protein.

6. A pharmaceutical composition comprising an effective amount of the factor of claim 1 and a pharmaceutically acceptable excipient or diluent.

7. The pharmaceutical composition of claim 6 which further comprises an effective dose of interleukin II, cytoxan or tumor necrosis factor.

* * * * *